(12) United States Patent
Wang et al.

(10) Patent No.: US 12,319,585 B2
(45) Date of Patent: Jun. 3, 2025

(54) METHOD FOR PRODUCING CALCIUM SULFATE HEMIHYDRATE WHISKERS BY USING FERMENTATION BROTH FOR PRODUCING LACTIC ACID WITH CALCIUM SALT METHOD AS RAW MATERIAL AND SYNCHRONOUSLY RECOVERING LACTIC ACID MONOMER

(71) Applicant: TIANJIN UNIVERSITY OF SCIENCE & TECHNOLOGY, Tianjin (CN)

(72) Inventors: Zhengxiang Wang, Tianjin (CN); Dandan Niu, Tianjin (CN); Kangming Tian, Tianjin (CN); Fuping Lu, Tianjin (CN); Chunli Shen, Tianjin (CN)

(73) Assignee: TIANJIN UNIVERSITY OF SCIENCE & TECHNOLOGY, Tianjin (CN)

( * ) Notice: Subject to any disclaimer, the term of this patent is extended or adjusted under 35 U.S.C. 154(b) by 110 days.

(21) Appl. No.: 17/616,648

(22) PCT Filed: Feb. 3, 2021

(86) PCT No.: PCT/CN2021/074953
§ 371 (c)(1),
(2) Date: Dec. 4, 2021

(87) PCT Pub. No.: WO2022/141739
PCT Pub. Date: Jul. 7, 2022

(65) Prior Publication Data
US 2024/0025756 A1    Jan. 25, 2024

(30) Foreign Application Priority Data

Dec. 31, 2020 (CN) .......................... 202011613171.3

(51) Int. Cl.
*C01F 11/46* (2006.01)
*C07C 51/42* (2006.01)

(52) U.S. Cl.
CPC .............. *C01F 11/46* (2013.01); *C07C 51/42* (2013.01); *C01P 2004/10* (2013.01)

(58) Field of Classification Search
CPC ......... C01F 11/46; C07C 51/42; C07C 51/02; C07C 51/47; C01P 2004/10; C01P 2004/01; C12P 7/56
See application file for complete search history.

(56) References Cited

U.S. PATENT DOCUMENTS

2003/0125581 A1 *   7/2003   Gerkema ................ C07C 51/44
562/589

FOREIGN PATENT DOCUMENTS

WO    WO1993024410 A1 *  12/1993  .............. C01F 11/46

* cited by examiner

*Primary Examiner* — Wayne A Langel
*Assistant Examiner* — Syed T Iqbal
(74) *Attorney, Agent, or Firm* — Jose Cherson Weissbrot

(57) ABSTRACT

The disclosure discloses a method for producing α-calcium sulfate hemihydrate whiskers by using fermentation broth for producing lactic acid with a calcium salt method as a raw material and synchronously recovering a lactic acid monomer. The method comprises the following steps: 1) after fermentation of lactic acid is ended, heating fermentation broth; 2) stirring, and adding sulfuric acid for reaction; 3) after the reaction is ended, filtering and collecting a solid part, namely α-calcium sulfite hemihydrate whiskers, and collecting a liquid part, namely a free lactic acid solution containing the lactic acid monomer; and 4) washing and drying the obtained α-calcium sulfate hemihydrate whiskers to obtain a α-calcium sulfate hemihydrate whisker finished product, filtering and concentrating the obtained free lactic acid solution to obtain a lactic acid crude product, and (Continued)

refining the lactic acid crude product to obtain a high-purity lactic acid monomer. The disclosure can replace the efficient separation of lactic acid in production of lactic acid with the existing calcium salt method and high value-added transformation of a calcium sulfite byproduct, thereby significantly reducing the refining cost of lactic acid and formation of wastes and facilitating improvement of lactic acid production quality and simplification of a post-extraction process technology.

9 Claims, 2 Drawing Sheets

METHOD FOR PRODUCING CALCIUM SULFATE HEMIHYDRATE WHISKERS BY USING FERMENTATION BROTH FOR PRODUCING LACTIC ACID WITH CALCIUM SALT METHOD AS RAW MATERIAL AND SYNCHRONOUSLY RECOVERING LACTIC ACID MONOMER

FIELD OF TECHNOLOGY

The disclosure belongs to the fields of fermentation engineering and chemical engineering, particularly relates to direct transformation of calcium lactate fermentation broth into α-calcium sulfate hemihydrate whiskers and free lactic acid in the presence of sulfuric acid when in production via lactic acid fermentation.

BACKGROUND

Lactic acid is an important three-carbon organic acid with two optical configurations: L form and D form, namely, L-lactic acid and D-lactic acid. Both of L-lactic acid and D-lactic acid are monomer raw materials for synthesis of polylactic acid, and are important components of biologically degradable materials. In addition, L-lactic acid and D-lactic acid can also be used as raw materials for synthesis of many esters (for example methyl lactate, ethyl lactate, propyl lactate and butyl lactate) and lactates. L-lactic acid, as an acidifying agent, can also be widely applied to production of products such as food, beverages, condiments, alcohol and animal feed. D-lactic acid can also be used as a raw material for synthesis of flavors and fragrances, herbicides, medicines and the like.

Lactic acid is produced mainly through microbial fermentation, in which a calcium salt method is the most important method for producing lactic acid via fermentation, that is, microbial strains metabolize an adaptive carbon source (such as glucose, glycerin, xylose, lactose, sucrose and fructose) into D-lactic acid or L-lactic acid via fermentation (Tian, et al., Biotechnology Bioengineering, 2016, 113: 181-188; Niu, et al., Microbial Cell Factories, 13: 78-88; Chen, et al., Green Chemistry, 16: 342-350; Zhou, et al., Metabolic Engineering, 14: 560-568; Chen, et al, Biotechnol Adv, 31:1200-1223, 2013; Kangming Tian, et al, Journal of Bioengineering, 29: 111-114, 2013; Kangming Tian, et al, Journal of Bioengineering, 29: 1-10, 2013; Zhengxiang Wang, et al, ZL201580000781.7). The produced lactic acid is transformed into calcium lactate while maintaining the pH of production through addition of calcium hydroxide or calcium carbonate during the fermentation, the formed calcium lactate is transformed into free lactic acid through addition of sulfuric acid after fermentation is ended, and water-insoluble calcium sulfate is generated and precipitated out from the solution in a form of amorphous dihydrate. The fermentation broth containing free lactic acid is subjected to refining of lactic acid through a series of procedures such as separation and purification to produce a lactic acid product. The formed water-insoluble calcium sulfate is a byproduct produced when in lactic acid fermentation (Peng Zhang, et al., ZL200810049644.4), which is used for producing calcium sulfate dihydrate through procedures such as separation and drying, namely raw gypsum.

In the calcium salt method of lactic acid fermentation production, calcium sulfate dihydrate (raw gypsum) is produced in a larger quantity, with a quality comparable to that of the lactic acid. The amount of calcium sulfate dihydrate (gypsum) is comparable to that of the lactic acid product. Since the calcium sulfate dihydrate (raw gypsum) has general physiochemical properties, it is currently applied to fabrication of food-grade gypsum, low-end cement additives, feed additives and the like in most cases, has a low application value, and even becomes a "solid waste", and is extremely disadvantageous to production of large-scale lactic acid (Fanfan Zhang, et al., INORGANIC SALT INDUSTRY, 2017, 49(8):10-13).

Further transformation of the raw gypsum into other products with better physicochemical properties is an important way to solve the problem of large-scale production of lactic acid with the calcium salt method, which can solve the generation problem of calcium sulfate dihydrate (raw gypsum) byproducts while ensuring the large-scale industrial production of lactic acid.

In the prior art, the raw gypsum is calcined and ground to obtain β hemihydrate gypsum ($CaSO_4 \cdot 0.5H_2O$), namely building gypsum, also known as plaster and mortar. The model gypsum can be obtained by increasing the calcination temperature to 190° C., and its fineness and whiteness are both higher than those of the building gypsum; when the calcination temperature is increased to 400° C.~500° C. or higher than 800° C., the raw gypsum can be transformed into floor gypsum, the floor gypsum is slowly coagulated and hardened, but the hardened floor gypsum has better strength, wear resistance and water resistance than those of the common building gypsum (Liqian Zhang et al., GREEN ENVIRONMENTAL PROTECTION BUILDING MATERIALS, 2020, (02): 14-15, 18). However, the above physical calcination solution in which the raw gypsum is transformed into β hemihydrate gypsum or sewage gypsum is not suitable for processing the calcium sulfate byproduct when lactic acid is produced via fermentation for the main reasons that the absolute generation amount of calcium sulfate dihydrate in the process of producing lactic acid via fermentation is relatively few, and the above product has a low added value and limited investment-income.

Recently, bran-new methods have been partially established in many researches, which can transform the raw gypsum into α-calcium sulfate hemihydrate whiskers (Ru Yang et al., ZL201910466020.0; Peiyang Shi et al., ZL201910373883.3; Hongyu Wang et al., ZL201610547294.9; Huafeng Zhou et al., SILICATE BULLETIN, 2017, 36:2090-2094; YISHUN CUI, CHEMICAL MINERALS AND PROCESSING, 2017, 46 (3): 13-16). The α-calcium sulfate hemihydrate whisker has many excellent physiochemical properties, such as high strength, high modulus, high toughness, high insulation, wear resistance, high temperature resistance, acid and alkali resistance, corrosion resistance, good infrared reflection, easy surface treatment and no toxicity, and is easily compounded with polymers and integrates the advantages of reinforced fibers and ultra-fine inorganic fillers, thus it has a high application value (Ming Li, FINE AND SPECIAL CHEMICALS, 2016, 24 (6): 47-50), and can be used as a reinforcing and toughening agent or a functional filler in resins, plastics, rubbers, coatings, paints, papermaking, asphalts, friction and sealing materials (Hang He et al., APPLIED CHEMICAL INDUSTRY, 2014:1671-1674; Maogang Li et al., SILICATE BULLETIN, 2017, 36:1590-1593; Jundai Li, JOURNAL OF EAST CHINA JIAOTONG UNIVERSITY, 2013, 30 (6): 72-77; LINGJIE FU ET AL., JOURNAL OF SICHUAN INSTITUTE OF TECHNOLOGY (NATURAL SCIENCE EDITION), 2013, 26 (5): 7-10; Pengfei Lv et al., CHEMICAL PROGRESS, 2013, 32:842-847890; Zehong Wang et al., MINING AND METALLURGY, 2005 (2): 38-41); it can also be directly used as a filter material, a thermal insulation material, a fire-resistant and thermal insulation material, an infrared reflection material and a high insulation material for covering wires (Mingjie Huang et al., FIRE RESISTANCE AND LIME, 2014, 39 (3): 19-20, 23; Mingjie Huang et al., MODERN COATINGS AND COATING, 2013, 16 (11): 18-19, 26).

The reported methods for transforming raw gypsum into α-calcium sulfate hemihydrate whiskers mainly include the following methods:

(1) Autoclave method: natural calcium sulfate dihydrate is crushed into blocks of 20~50 mm and put into an autoclave through a metal frame or a trolley. The autoclave methods include a vertical autoclave method and a horizontal autoclave method. Stream condensate water or hot fume is introduced to heat the material to 50~70° C., the condensate water or hot fume is discharged, the autoclave is sealed, then saturated steam is introduced to raise the temperature to 120~160° C. and the pressure is maintained, and the calcium sulfate dihydrate is transformed into α-calcium sulfate hemihydrate whiskers after autoclave dehydration for 5~8 h, and the α-calcium sulfate hemihydrate whiskers are discharged from the autoclave to be dried or dried in the autoclave. The production cycle of the vertical autoclave is about 16~18 h and the production cycle of the horizontal autoclave is about 30~40 h (Qingyu Geng et al., JOURNAL OF SYNTHETIC CRYSTALS, 2016, 45:1892-1897; Lin Yang et al., JOURNAL OF BUILDING MATERIALS, 2014, 17:147-152; Hongyu Wang et al., ZL201610547294.9; Xueying Nai et al., ZL201610547294.9). This method is a traditional process, which is simple in process, long in production period and high in production cost, and the dehydration, crystal formation and drying of block raw materials are uneven due to uneven heating so as to result in great product quality fluctuation, and low product strength, generally about 20~30 MPa.

(2) Hydrothermal method: natural calcium sulfate dihydrate is ground into fine powder, the fine powder is added into an aqueous solution containing a crystal transformation promoter to be prepared into a suspension in which the solid content is generally no more than 30%. The suspension is added into a vertical autoclave, the suspension is continuously stirred and heated at the same time, and water is evaporated to form steam and generate a pressure to form autoclave conditions. After the reaction is carried out for about 5~8 h under the condition that the autoclave reaches an autoclave condition of 120~180° C., the dehydration and crystal transformation processes are completed, then the gas is exhausted and the pressure is dropped, and then a finished product is obtained by dehydration, washing, drying and grinding. After crushing and grinding, the obtained powder is mixed with water to be prepared into slurry, some additives or crystal transformation agents that can promote the crystallization and transformation are added, then the slurry is added into the autoclave with a steam jacket. The steam is introduced into the jacket for heating while stirring, and dihydrate gypsum is transformed into well crystallized gypsum α-calcium sulfate hemihydrate whiskers. Then the steam is discharged and the pressure is dropped, the slurry is discharged and then dehydrated, washed, dried and ground to prepare the high-strength α gypsum powder. The α-calcium sulfate hemihdyrate produced by this method is stable in product quality, and high in compressive strength, which can reach 40~80 MPa (Na Tang et al., INORGANIC SALT INDUSTRY, 2020, 52 (4): 88-92; Feng Wu et al., CHEMICAL PROGRESS, 2018, 37:1536-1543; Xu Huang et al., SILICATE BULLETIN, 2019, 38:2021-2027; Zirui Zhang et al., NINGXIA ENGINEERING TECHNOLOGY, 2019, 18:40-43, 49; Yubin Wang et al., JOURNAL OF CHEMICAL ENGINEERING OF COLLEGES AND UNIVERSITIES, 2018, 32:1444-1449; Xianhong Liang et al., MINERAL PROTECTION AND UTILIZATION, 2017 (06): 87-92, 96; Wu M, WO2015/085133 A1). However, this method is complicated in process, many in production equipment, large in investment, small in production capability, low in production efficiency and high in production cost, and cannot directly integrated into a fermentation and production process of lactic acid.

(3) Normal-pressure salt solution method: the ground calcium sulfate dihydrate is mixed with a salt solution added with a crystal transformation agent, and the resulting mixture is added into a reaction vessel and boiled under the normal pressure, so that the calcium sulfate dihydrate is transformed into α-calcium sulfate hemihydrate whiskers. The α-calcium sulfate hemihydrate whiskers are obtained by dehydration, washing and drying. This method does not need pressure vessels and can reduce equipment investment (Aiwen Wang et al., NONMETALLIC MINERALS, 2020, 43 (4): 84-87; Haiyong Zhang, CHEMICAL MINERALS AND PROCESSING, 2020, 49 (1): 50-54; Wenjian Fu et al., JOURNAL OF EAST CHINA UNIVERSITY OF TECHNOLOGY (NATURAL SCIENCE EDITION), 2019, 45 (2): 266-274; Junyao Hu et al., INORGANIC SALT INDUSTRY, 2018, 50 (6): 47-50; Xin Wang et al., INORGANIC SALT INDUSTRY, 2017, 49 (11): 54-58). However, this method is strict in process conditions, long in reaction time and low in product strength. At present, this method is still in the laboratory test stage, and there are no examples for industrial production.

(4) Normal-pressure glycerol method: industrial byproduct calcium sulfate dihydrate is added into a 45%~75% glycerol solution, a certain amount of crystal regulator is added, the reaction is maintained for 30 min at 90° C., and the α-calcium sulfate hemihydrate whiskers are obtained by filtration, washing and drying. This method does not need a high-pressure environment, mild in action conditions and high in product purity. However, the prepared α-calcium sulfate hemihydrate whisker has short length and small hardness (Qingjun Guan et al., MINERAL PROTECTION AND UTILIZATION, 2019, 39 (4): 1-8). At present, this method is in the laboratory test stage, and there are no production examples.

All of the above preparation methods of α-calcium sulfate hemihydrate whiskers use calcium sulfate dihydrate as a starting raw material. Most of the production processes need to be carried out at a temperature of higher than 120° C. Parts of methods also need to add different compounds, which not only increases the manufacturing cost, but also increases the byproducts. Accordingly, the existing production technology of α-calcium sulfate hemihydrate whiskers cannot directly prepare the α-calcium sulfate hemihydrate whiskers while preparing lactic acid monomers from fermentation broth with a calcium salt method. In addition, too high reaction temperature and addition of a crystal transformation agent can significantly affect the recovery of lactic acid monomers.

So far, the processes of releasing lactic acid in calcium lactate generated in the process of producing lactic acid with a calcium salt method are based on the formation of calcium sulfate byproduct, and cannot realize synchronization of release of lactic acid and preparation of α-calcium sulfate hemihydrate whiskers, and needs to further treat calcium sulfate "solid waste" in the subsequent production, which not only increases the production cost, but also makes the production process not green and environmental friendly. It can be seen that synchronous production of lactic acid monomer and α-calcium sulfate hemihydrate whiskers, on one hand, can intensify the lactic acid production process and reduce the lactic acid production inputs, and on the other hand, can completely solve the problem of formation of the calcium sulfate waste in the existing industrial production system. Therefore, the economic benefits and environmental benefits of lactic acid fermentation production are remarkably improved and the comprehensive cost of lactic production can be greatly reduced, which is of great significance to promote the technological progress of lactic acid monomer fermentation industry and the healthy development of polylactic acid industry chain.

SUMMARY

The objective of the disclosure is to directly release free lactic acid from calcium lactate fermentation broth in the production of lactic acid via fermentation with a calcium salt method and meanwhile directly generate replaced calcium sulfate in a form of α-calcium sulfate hemihydrate whiskers, so as to realize the synchronous production of lactic acid monomers and α-calcium sulfate hemihydrate whiskers.

In order to realize the above objective, the technical solution provided by the disclosure is as follows:

A method for producing α-hemihydrate calcium sulfate whiskers from fermentation broth of lactic acid production by calcium salt method and simultaneous recovery of lactic acid monomer, comprising the steps of:

Step 1: after the lactic acid fermentation is finished, transferring the fermentation solution into the extraction reactor and raising the temperature to 50° C.~102° C. in place or in a post-extraction reactor;

Step 2: adding 2~12 mol/L sulfuric acid to the solution in step 1, maintaining the temperature constant, and reacting for 1 min~10 h;

Step 3: after the reaction in Step 2 is ended, filtering a reaction solution for solid-liquid separation, collecting a solid part, namely α-calcium sulfate hemihydrate whiskers, and collecting a liquid part, namely free lactic acid solution containing the lactic acid monomer; wherein, further, the described solid-liquid separation is carried out by using a belt filter with a pore size of 5.0 μm~50 μm;

Step 4-1: washing and drying the obtained α-calcium sulfate hemihydrate whiskers to obtain a α-calcium sulfate hemihydrate whisker finished product; wherein, further, the described α-calcium sulfate hemihydrate whisker is washed with hot water or absolute ethyl alcohol and subjected to flash drying with the steam of 101° C.~160° C., so as to obtain the α-calcium sulfate hemihydrate whisker end-product;

Step 4-2: filtering and concentrating the obtained free lactic acid solution to obtain a lactic acid crude product which can be used for subsequent refining such as nanofiltration, decolorization and ion exchange to obtain a high-purity lactic acid monomer; wherein, further, the obtained free lactic acid solution is filtered in a plate frame with a pore size of 0.8 μm~10 μm to remove impurities, and then evaporated and concentrated until the content of lactic acid is 20 wt %~60 wt %, so as to obtain the lactic acid crude product.

Rising the temperature in step 1 to 55° C.-102° C., further to 60° C.-102° C., further to 65° C.-102° C., further to 70° C.-102° C., further to 75° C.-102° C., further to 80° C.-102° C., further to 85° C.-102° C.

The reaction in step 2 is carried out at a stirring speed of 5 to 80 r/min and the reaction temperature of step 1 is maintained. The total amount of sulfuric acid added is controlled at a molar ratio of 1:0.499 to 1:0.501 of lactic acid to sulfuric acid, and the total time limit of sulfuric acid addition is controlled from 1 minute to 2 hours per ton of fermentation broth, and the reaction is maintained from 1 minute to 10 hours after all sulfuric acid was added.

According to the method, the recovery rate of the lactic acid monomer can reach 99.5% or more, and the recovery rate of calcium sulfate and the generation rate of the α-calcium sulfate hemihydrate whiskers reach 98% or more.

The disclosure has the beneficial effects:

In the disclosure, the lactic acid solution can be transformed into free lactic acid and α-calcium sulfate hemihydrate whisker in one step using a calcium salt method, so as to realize the synchronous production of lactic acid monomers and α-calcium sulfate hemihydrate whiskers, the recovery rate of the lactic acid monomer reaches 99.5% or more, the recovery rate of calcium sulfate and the generation rate of the α-calcium sulfate hemihydrate whiskers reach 98% or more, which, on one hand, can intensify the lactic acid production process and reduce the lactic acid production inputs, and on the other hand, can completely solve the problem of formation of the calcium sulfate waste in the existing industrial production system. Therefore, the economic benefits and environmental benefits of lactic acid fermentation production are remarkably improved and the comprehensive cost of lactic production can be greatly reduced. The method of the disclosure can also be applied to generation of other organic acids such as citric acid, malic acid and succinic acid after being simply modified.

In the disclosure, when lactic acid in calcium lactate is treated with sulfuric acid via transformation, it is found that amorphous calcium sulfate dihydrate that is originally generated is transformed into α-calcium sulfate hemihydrate whiskers in this process as long as a certain temperature is given and the subsequent separation refining is not influenced, and the addition speed of sulfuric acid is controlled. The key points of this process are temperature and sulfuric acid addition speed, wherein the temperature cannot be too high like the temperature described in the existing document, lactic acid can be greatly lost if the temperature exceeds 105° C., and lactic acid is a main product; and any crystal transformation agent or crystal promotion agent cannot be added, because it can increase the separation and refining cost of lactic acid.

DESCRIPTION OF THE EMBODIMENTS

To make the purpose, technical solution and advantages of this patent clearer, this patent will be further described in detail in combination with specific embodiments. It should be understood that the specific embodiments described herein are only for explaining this patent, but are not intended to limit the disclosure.

Figure 1:
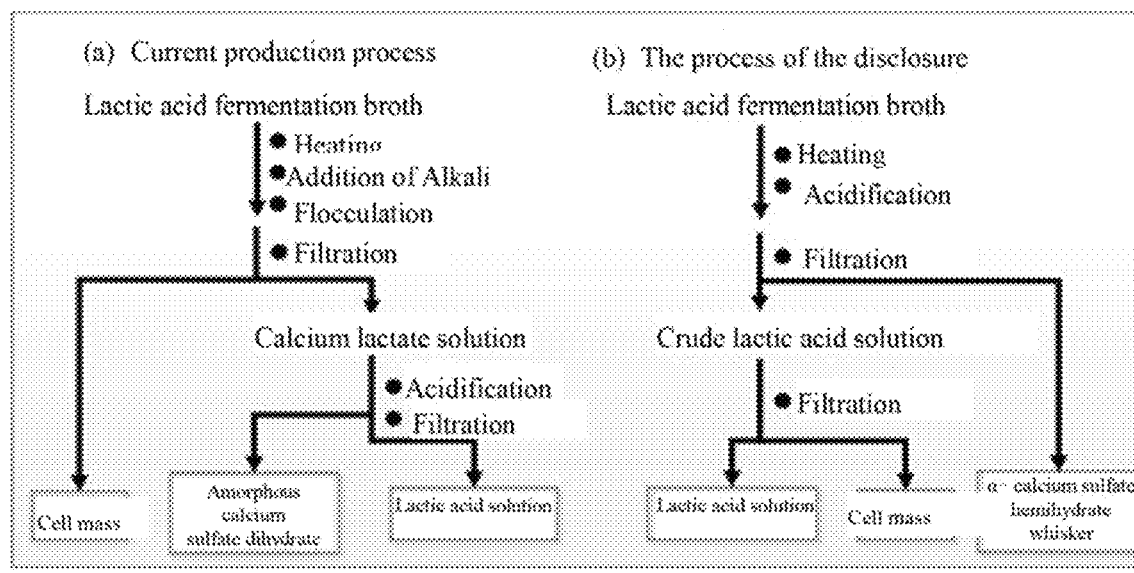
FIG. 1 shows a process route for production of lactic acid: (a) original production process; (b) the process of the disclosure.
Figure 2:
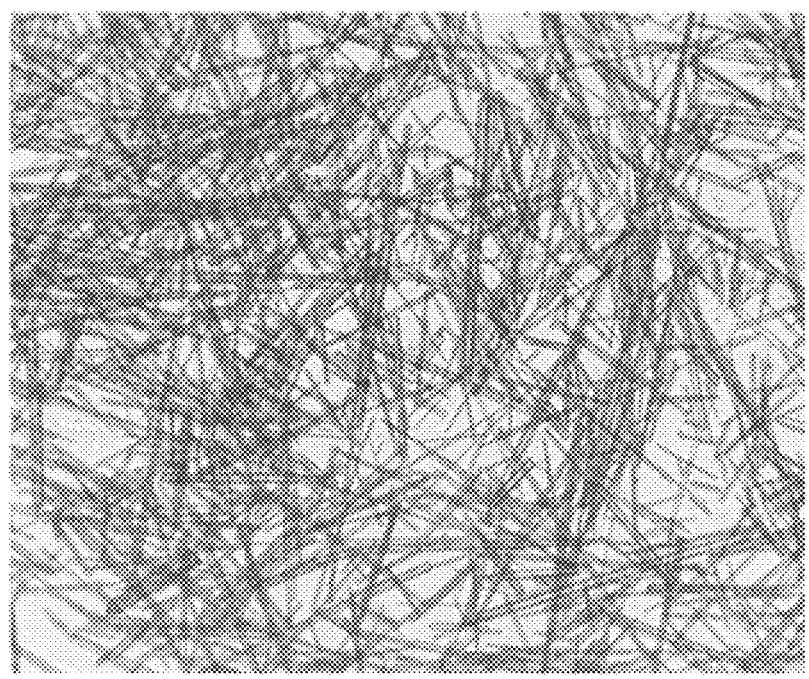
FIG. 2 is a morphology image of α-calcium sulfate hemihydrate whiskers (100X).

In the disclosure, fermentation broth for producing lactic acid with a calcium salt method is used as a raw material, after fermentation of lactic acid is ended, fermentation broth is heated to 50° C.~102° C., 2~12 mol/L sulfuric acid is added and the reaction is maintained for 1 min~10 h, then solid-liquid separation is carried out through filtration, a solid part, namely α-calcium sulfate hemihydrate whiskers, is collected and a liquid part, namely free lactic acid solution containing the lactic acid monomer, is collected. The obtained α-calcium sulfate hemihydrate whiskers are washed and dried to obtain a α-calcium sulfate hemihydrate whisker end-product, the obtained free lactic acid solution is filtered and concentrated to obtain a lactic acid crude product, and the obtained lactic acid crude product can be subjected to subsequent refining such as nanofiltration, decoloration and ion exchange to obtain a high-purity lactic acid monomer (FIG. 1).

The main experiment methods adopted by the disclosure are as follows:

1. Preparation of Lactic Acid Fermentation Broth with a Calcium Salt Method

The preparation of lactic acid fermentation broth with the calcium salt method was carried out according to a method of the authorized patent of the previous invention (Zhengxiang Wang et al., ZL201580000781.7). The fermentation strain is CGMCC11059 or CGMCC11060, in which the strain CGMCC11059 was used for fermentation production of D-lactic acid and the strain CGMCC11060 was used for fermentation production of L-lactic acid (Zhengxiang Wang et al., ZL201580000781.7). In the initial stage of fermentation, glucose was added to a basic fermentation medium so that the final concentration was 10~50 g/L, and the culture was carried out by stirring under the conditions of 30° C.~37° C., pH 5.5~7.5, ventilation 0.1~2.0 vvm and 100~1000 r/min; the culture time was 5~15 h, and the quantity of bacteria reached 10~50 OD; the ventilation was closed, the stirring speed was reduced to 0~300 r/min, the fermentation temperature was increased to 37° C.~50° C., a glucose solution with a final concentration of 16%~25% was supplemented, the flow rate was controlled at 3 g/(L·h)~25 g/(L·h), 5%~35% calcium hydroxide was synchronously added, and the fermentation pH was controlled between 5.0 and 8.0.

2. Acidification of Fermentation Broth and Preparation of α-calcium Sulfate Whiskers After fermentation, the fermentation broth was warmed up to 50° C.~102° C., stirring was turned on, 2~12 mol/L sulfuric acid was added, the total amount of sulfuric acid added was controlled at the molar ratio of lactic acid to sulfuric acid of 1:0.499~1:0.501, the time of sulfuric acid addition was controlled at 1 min~2 h/ton of fermentation broth, and the reaction was maintained for 1 min~10 h after addition.

3. Separation of Lactic Acid and α-calcium Sulfate Hemihydrates Whiskers

After the reaction was ended, the reaction solution was filtered for solid-liquid separation, and the solid-liquid separation was carried out by using a belt filter with a pore size of 5.0 μm~50 μm was used, a solid part, namely α-calcium sulfate hemihydrate whiskers, was collected, a liquid part, namely free lactic acid solution containing lactic acid monomers, was collected.

4. Refining of α-calcium Sulfate Hemihydrates Whiskers

The obtained α-calcium sulfate hemihydrate whiskers were washed with hot water or absolute ethyl alcohol and dried, and then subjected to flash drying via 101° C.~160° C. steam to obtain a α-calcium sulfate hemihydrate whisker finished product.

5. Analysis on Morphology of α-calcium Sulfate Hemihydrates Whiskers

The appearance of whiskers was observed and recorded under an optical microscope. The lengths and diameters of 40 whiskers were measured, and their length diameter ratios were calculated. All the data are average values of 3 parallel test results.

6. Yield of α-calcium Sulfate Hemihydrate Whiskers

The yield of α-calcium sulfate hemihydrate whiskers can be expressed as a ratio of actual value to theoretical value. The actual value is the mass of the α-calcium sulfate hemihydrate whisker finished product. The theoretical value is the weight of α-calcium sulfate hemihydrate whiskers calculated according to the mole of sulfuric acid added when in acidification. The mole of sulfuric acid is equal to that of α-calcium sulfate hemihydrate whiskers, the product of the mole of sulfuric acid and the relative molecular mass of the α-calcium sulfate hemihydrate whiskers is the theoretical value of the whiskers, based on %.

7. Content, Mass and Yield of Lactic Acid

Determination of contents of D-lactic acid, L-lactic acid, pyruvic acid, formic acid, acetic acid and succinic acid: HPLC is used. The chromatographic detection conditions are as follows: the chromatographic column is HPX-87H organic acid analysis column, the column temperature is 65° C., the detection wavelength is 210 nm, the mobile phase is 5 mmol/L sulfuric acid solution, the flow rate is 0.8 mL/min, and the injection volume is 10 μL. All the data are the average values of 3 parallel test results. The content of the lactic acid monomer is calculated in g/L, and the chemical purity of lactic acid is calculated as the percentage (%) of lactic acid monomer in all the organic acids. The sugar-acid conversion rate of lactic acid is calculated as the percentage (%) of total lactic acid production mass in total glucose consumption.

Determination of optical purity of lactic acid monomer: HPLC is used. The chromatographic detection conditions are as follows: the chromatographic column is AstecCLC-L optical purity analysis column, the column temperature is 25° C., the detection wavelength is 254 nm, the mobile phase is 5 mmol/L copper sulfate solution, the flow rate is 1 mL/min, and the injection volume is 10 μL. All the data are the average values of 3 parallel test results. The optical purity of the lactic acid monomer is calculated as the mass percentage (%) of L-lactic acid or D-lactic acid in total lactic acid.

Calculation of calcium lactate concentration: the content of the above free lactic acid is converted into the content of calcium lactate according to the molar ratio, that is, 1 mole of calcium lactate is formed by combining 2 moles of free lactic acid with a calcium salt.

Example 1: Preparation of Lactic Acid Fermentation Broth

The glycerol tube frozen storage materials of D-lactic acid production strain CGMCC11059 or L-lactic acid production strain CGMCC11060 were inoculated into a 50 mL LB liquid culture medium to be subjected to shake cultivation for 12 h under 37° C. at 200 r/min as a primary seed solution. The primary seed solution was inoculated into a 150 mL M9 liquid culture medium with glucose as a carbon source. The initial sugar concentration was 0.5%, the inoculated primary seed solution was subjected to shake cultivation for 10 h under 37° C. at 200 r/min as a secondary seed solution. The secondary seed solution was inoculated into a fermentation tank containing the M9 liquid culture medium in an inoculation amount being 0.3 of the initial OD value. After inoculation, the initial volume of the 50 L fermentation tank was 25 L, and the initial addition amount of conversion syrup was 3%, the fermentation production of the lactic acid monomer was started. The initial fermentation temperature is controlled at 37° C., and pH 6.5 was maintained with ammonia. In the process of cell growth, the ventilation amount was adjusted to up to 1.5 vvm through adjustment and the stirring speed was up to 1000 r/min. When the cell concentration reached $OD_{600}$ 30, the ventilation was closed, the fermentation temperature was controlled at 40° C., the stirring speed was adjusted to 200 r/min, 25% calcium hydroxide turbid liquid was added to maintain pH 7.0, 6.0 kg of total glucose was supplemented, and the fermentation was ended after the concentration of residual glucose was lower than 0.5 g/L. The crucial fermentation results are summarized in Table 1.

TABLE 1

Preparation of lactic acid monomer fermentation broth and its main parameters

| Fermentation index | Summary of fermentation data | |
|---|---|---|
| | D-lactic acid | L-lactic acid |
| Concentration of calcium lactate (g/L) | 167 | 169 |
| Chemical purity (%) | 98.2 | 98.5 |
| Optical purity (%) | 99.96 | 99.98 |
| Conversion rate (%) of sugar-acid | 92.1 | 93.4 |
| Final fermentation volume (L) | 39 | 41 |

Example 2: Preparation of α-calcium Sulfate Hemihydrate Whiskers

The lactic acid fermentation broth obtained in example 1 above was heated to 88° C. in a reactor and this temperature was maintained. The 5 mol/L sulfuric acid solution was added by stirring at the rotation speed of 20 r/min. The total amount of sulfuric acid was controlled at a molar ratio of lactic acid to sulfuric acid of 1:0.5, and the time limit of the whole sulfuric acid solution added was controlled at 1 h/ton of fermentation broth; after the whole sulfuric acid solution was added, the reaction was maintained for 15 min; after the reaction was ended, the solid-liquid separation of the reaction solution was carried out by using a belt filter with a pore size of 8.0 λm, and a solid part was collected, namely α-calcium sulfate hemihydrate whiskers, the obtained α-calcium sulfate hemihydrate whisker was washed with absolute ethyl alcohol and subjected to flash drying with 120° C. steam so as to obtain the α-calcium sulfate hemihydrate whisker finished product; a liquid part was collected, namely free lactic acid solution containing the lactic acid monomer, the free lactic acid solution was filtered in a plate frame with a pore size of 6 μm to remove impurities, then evaporated and concentrated until the content of lactic acid was 20 wt %~60 wt %, so as to obtain a lactic acid crude product. The lactic acid crude product was subjected to ion exchange, activated carbon decolorization, ultrafiltration and other refining processes to obtain a high-purity lactic acid monomer. According to the method, the generation rate of α-calcium sulfate hemihydrate whisker reaches 98% or more (Table 2), the calcium sulfate whisker was of α type, the length-to-radius of the whisker was 13.2~130.2, and the length-to-radius of the 80% whisker was 54.3~85.0 (Table 3), and the recovery rate of the lactic acid monomer reached 99.5% or more (Table 4).

TABLE 2

Generation rate of α⁻ calcium sulfate hemihydrate whiskers

| Batches | Generation rate of whiskers (%) |
|---|---|
| Batch 1 | 98.62 |
| Batch 2 | 98.14 |
| Batch 3 | 99.33 |
| Batch 4 | 99.51 |
| Batch 5 | 98.92 |
| Batch 6 | 99.36 |

TABLE 3

Length-to-radius ratios of α⁻ calcium sulfate hemihydrate whiskers

| Batches | Range of length-to-radius ratio of whiskers | Range of length-to-radius ratio of 80% whiskers |
|---|---|---|
| Batch 1 | 22.1-124.3 | 60.2-80.6 |
| Batch 2 | 13.2-122.4 | 59.7-85.0 |
| Batch 3 | 20.3-128.4 | 55.6-83.5 |
| Batch 4 | 30.4-129.6 | 54.3-82.6 |
| Batch 5 | 14.8-130.2 | 59.3-80.7 |
| Batch 6 | 16.7-127.8 | 57.8-79.5 |

TABLE 4

Recovery rate of lactic acid monomer

| Batches | Recovery rate (%) of lactic acid monomers |
|---|---|
| Batch 1 | 99.64 |
| Batch 2 | 99.58 |
| Batch 3 | 99.63 |
| Batch 4 | 99.59 |
| Batch 5 | 99.70 |
| Batch 6 | 99.82 |

The above descriptions are only preferred embodiments of the disclosure. Equivalent changes and modifications made according to the patent scope of the present invention application shall be included within the coverage scope of the disclosure.

What is claimed:

1. A method for producing α-calcium sulfate hemihydrate whiskers by using fermentation broth for producing lactic acid with a calcium salt method as a raw material and synchronously recovering a lactic acid monomer, comprising the following steps:
    Step 1: after fermentation of lactic acid is ended, heating fermentation broth;
    Step 2: stirring, and adding sulfuric acid under the condition of maintaining the temperature of step 1 for reaction;
    Step 3: after the reaction is ended, filtering a reaction solution for solid-liquid separation, and collecting a solid part, namely α-calcium sulfate hemihydrate whiskers, and collecting a liquid part, namely a free lactic acid solution containing the lactic acid monomer;

Step 4-1: washing and drying the obtained α-calcium sulfate hemihydrate whiskers to obtain a α-calcium sulfate hemihydrate whisker finished product;

Step 4-2: filtering and concentrating the obtained free lactic acid solution to obtain a lactic acid crude product, and refining the lactic acid crude product to obtain a lactic acid monomer having a chemical purity over 98% and an optical purity over 99.5%, wherein the recovery rate of the lactic acid monomer is above 99.5%.

2. The method according to claim 1, wherein the fermentation broth in Step 1 is heated to 50° C.~102° C.

3. The method according to claim 2, wherein the fermentation broth in Step 1 is heated to 85° C.~102° C.

4. The method according to claim 1, wherein after fermentation of lactic acid in Step 1 is ended, heating is carried out in place or in a post-extraction reactor.

5. The method according to claim 1, wherein the reaction in Step 2 is maintained at a stirring speed of 5~80 r/min.

6. The method according to claim 1, wherein the concentration of sulfuric acid added in Step 2 is 2 mol/L~12 mol/L, a total amount of sulfuric acid is controlled at a molar ratio of lactic acid to sulfuric acid of 1:0.499~1:0.501, a time limit of total sulfuric acid added is controlled to 1 min~2 h per ton of fermentation broth, and the reaction is maintained for 1 min~10 h after the whole sulfuric acid is added.

7. The method according to claim 1, wherein the solid-liquid separation in Step 3 is carried out by using a belt filter with a pore size of 5.0 μm~50 μm.

8. The method according to claim 1, wherein the α-calcium sulfate hemihydrate whiskers in Step 4-1 are washed with absolute ethyl alcohol, and then subjected to flash drying through 101° C.~160° C. steam to obtain the α-calcium sulfate hemihydrate whisker finished product.

9. The method according to claim 1, wherein the obtained free lactic acid solution in Step 4-2 is filtered in a plate frame with a pore size of 0.8 μm~10 μm to remove impurities, and then evaporated and concentrated until the content of lactic acid is 20 wt %~60 wt %, so as to obtain a lactic acid crude product.

* * * * *